(12) United States Patent
Qi et al.

(10) Patent No.: US 9,192,638 B2
(45) Date of Patent: Nov. 24, 2015

(54) PREPARATION COMPRISING AMINO ACIDS AND PLANTS AND ITS ACTIVITY IN THE ALCOHOL DETOXIFICATION

(71) Applicants: Youmao Qi, Zhejiang (CN); Qing Jie, Zhejiang (CN); Fengmin Zhang, Zhejiang (CN); Ying Gu, Zhejiang (CN); Meiping Yu, Zhejiang (CN)

(72) Inventors: Youmao Qi, Zhejiang (CN); Qing Jie, Zhejiang (CN); Fengmin Zhang, Zhejiang (CN); Ying Gu, Zhejiang (CN); Meiping Yu, Zhejiang (CN)

(73) Assignees: Modutech S.A., Villars-sur-Glane (CH); Hangzhou Adamerck Pharmlabs Inc., Hangzhou (CN)

( * ) Notice: Subject to any disclaimer, the term of this patent is extended or adjusted under 35 U.S.C. 154(b) by 0 days.

(21) Appl. No.: 14/245,355

(22) Filed: Apr. 4, 2014

(65) Prior Publication Data

US 2014/0220162 A1    Aug. 7, 2014

Related U.S. Application Data

(62) Division of application No. 13/504,756, filed as application No. PCT/IB2010/054885 on Oct. 28, 2010.

(30) Foreign Application Priority Data

Oct. 28, 2009   (WO) ................. PCT/IB2009/007253

(51) Int. Cl.

| | | |
|---|---|---|
| *A61K 36/25* | (2006.01) | |
| *A61K 36/16* | (2006.01) | |
| *A61K 36/00* | (2006.01) | |
| *A61K 36/28* | (2006.01) | |
| *A23L 1/30* | (2006.01) | |
| *A23L 1/305* | (2006.01) | |
| *A61K 9/08* | (2006.01) | |
| *A61K 9/20* | (2006.01) | |
| *A61K 31/198* | (2006.01) | |
| *A61K 31/405* | (2006.01) | |
| *A61K 36/258* | (2006.01) | |
| *A61K 36/815* | (2006.01) | |
| *A61K 36/82* | (2006.01) | |
| *A61K 45/06* | (2006.01) | |
| *A61K 31/357* | (2006.01) | |

(52) U.S. Cl.
CPC .............. *A61K 36/28* (2013.01); *A23L 1/3002* (2013.01); *A23L 1/3051* (2013.01); *A61K 9/08* (2013.01); *A61K 9/2054* (2013.01); *A61K 31/198* (2013.01); *A61K 31/357* (2013.01); *A61K 31/405* (2013.01); *A61K 36/16* (2013.01); *A61K 36/258* (2013.01); *A61K 36/815* (2013.01); *A61K 36/82* (2013.01); *A61K 45/06* (2013.01); *A23V 2002/00* (2013.01)

(58) Field of Classification Search
CPC ..... A61K 36/258; A61K 36/25; A61K 36/16; A61K 36/00
See application file for complete search history.

(56) References Cited

U.S. PATENT DOCUMENTS

| 4,871,763 | A | 10/1989 | Madaus et al. | |
|---|---|---|---|---|
| 2003/0180395 | A1* | 9/2003 | Bueter | .......................... 424/725 |
| 2005/0019427 | A1 | 1/2005 | Langeland | |
| 2008/0160001 | A1 | 7/2008 | Ye et al. | |

FOREIGN PATENT DOCUMENTS

| CN | 1166320 A | 12/1997 |
|---|---|---|
| CN | 1188800 A | 7/1998 |
| CN | 1451426 A | 10/2003 |
| CN | 1535617 A | 10/2004 |
| CN | 1569123 A | 1/2005 |
| CN | 1660188 A | 8/2005 |
| CN | 1660188 A * | 8/2005 |
| CN | 1698879 A | 11/2005 |
| CN | 101053407 A | 10/2007 |
| CN | 101053407 A * | 10/2007 |
| DE | 19929993 A1 | 1/2001 |
| WO | WO-9947148 A1 | 9/1999 |
| WO | WO 9947148 A1 * | 9/1999 |
| WO | WO 9961038 A1 | 12/1999 |
| WO | WO-0212882 A2 | 2/2002 |
| WO | WO 0212882 A2 * | 2/2002 |

OTHER PUBLICATIONS

Qi, Y. Foreign Patent: CN 1451426 A, English Translation. Publication Date: Oct. 29, 2003.*
"L-Ornithine HCl". Internet Archive Date: Aug. 30, 2009 [Retrieved from the Internet on: Jan. 30, 2014]. Retrieved from: <URL: https://web.archive.org/web/20090830073139/http://supplementdirect.com/I-ornithinehcl250grams.aspx>.*

(Continued)

*Primary Examiner* — Patricia A Leith
(74) *Attorney, Agent, or Firm* — Oliff PLC

(57) ABSTRACT

The invention relates to a preparation containing several amino acids and plant extracts and its alcohol detoxification activity. The component (a) in the preparation contains a mixture of two or more amino acids or derivatives thereof; the component (b) in the preparation contains a mixture of three or more extracts from plants. There are several plant extracts used in this invention such as the extract of *ginseng* radix, the extract of *ginkgo biloba* leaf, the extract of Silibinin, the extract of barberry wolfberry fruit and tea polyphenosis. The invention also relates to the biological activities of said preparation, such as the liver protection from chemical injury, the tolerance enhancement of hypoxy and the rapid decrease till elimination of the blood alcohol content.

8 Claims, No Drawings

(56) References Cited

OTHER PUBLICATIONS

Healthline, Online, URL: http://www.healthline.com/health/cerebral-hypoxia#Causes2> 4 pages, accessed on Aug. 1, 2014.*
H.B. MacPhillamy: Drugs From Plants; Plant Science Bulletin, Botanical Society of America, vol. 9, No. 2, Apr. 1963.*
Phillipson, J. New Drugs From Nature—It Could Be Yew; Phytotherapy Research 13 (1999) pp. 2-8.*
Smet et al. Herbal Remedies; N Engl J Med, vol. 347, No. 25, Dec. 19, 2002, pp. 2046-2056.*
Raskin et al. Can an Apple a Day Keep the Doctor Away? Current Pharmaceutical Design, 2004, 10, 3419-3429.*
Revilla et al. Comparison of Several Procedures Used for the Extraction of Anthocynains From Red Grapes; J. Agric. Food Chem. 1998, 46, pp. 4592-4597.*
Wang et al. Recent Advances in Extraction of Neutraceuticals From Plants; Trends in Food Science & Technology 17 (2006) pp. 300-312.*
Chinese Pharmacopoeia; Kuang, L and Zhang, Ke, ed. 2005, pp. 322 and 323.*
International Search Report.
"L-Ornithine HCl". Internet Archive Date Aug. 30, 2009 [Retrieved from the Internet on: Jan. 30, 2014]. Retrieved from: <URL: https://web.archive.org/web/20090830073139/http://supplementdirect.com/l-ornithinehcl250grams.aspx>.
Jul. 2, 2015 Office Action issued in U.S. Appl. No. 13/504,756.

* cited by examiner

PREPARATION COMPRISING AMINO ACIDS AND PLANTS AND ITS ACTIVITY IN THE ALCOHOL DETOXIFICATION

CROSS-REFERENCE TO RELATED APPLICATIONS

The present application is a divisional application under 35 U.S.C. §121 of U.S. application Ser. No. 13/504,756, filed Apr. 27, 2012, which is a national stage application under 35 U.S.C. 371 of International Application No. PCT/IB2010/054885, filed Oct. 28, 2010, which claims priority under 35 U.S.C. §365 to PCT/1132009/007253, filed Oct. 28, 2009.

FIELD OF THE INVENTION

The invention relates to preparations for dietary, food supplement or medical purposes and more specifically to a preparation or a composition comprising amino acids and several plant extracts and its activity in the alcohol detoxification. The composition of the invention can be used in the protection of chemical liver injury, in hypoxic tolerance enhancement, in the in vivo ethanol content quickening removal and the reduction and viability enhancement in the anoxic environment.

BACKGROUND OF THE INVENTION

It is known that L-ornithine and citrulline are involved in at least three important annular metabolic pathways in the human body. The three metabolic pathways are respectively the urea circulation, the citric acid circulation and the nitric oxide circulation. By taking L-ornithine and citrulline, the endogenous biomolecular messenger nitrogen monoxide (NO) can be obtained through the related metabolic pathway. The blood circulation system in the human body cannot function without the vasodilation function of NO, the endogenous NO has the adjustment and control function on multiple physiological functions, for example, the energy among nerve synapses can be adjusted; and the learning and memorization process can be adjusted, etc.

The endogenous NO in the human body is generated by catalyzing L-arginine (L-Arg) to be decomposed by nitric oxide synthetase (NOS). L-Arg is an important substance in the human body, in addition to the NO generation and the participation in protein synthesis, L-Arg is also the precursor of urea, praline, agmatine, polyamine and the like and can stimulate the secretion of hormone, such as auxina and insulin to directly influence the health of the human body. When the human body is under special stress conditions, for example, under hypoxia condition, the endogenous NO in the human body is insufficient, which can cause altitude reaction or sickness.

Besides the effects of altitude reaction and ischemia-reperfusion injury prevention and treatment and cardio-cerebralvascular system and immune system protection, L-Arg can prolong the mice burden swimming time and reduce the accumulation of lactic acid caused by anaerobic glycolysis, therefore to perform the anti-fatigue function.

However, because the half-life period of the taken L-arginine (L-Arg) is very short (only approximately one hour) the direct replenishment of arginine cannot effectively increase the arginine concentration in the blood and the cells.

It is known that L-citrulline (L-cit) is a non-protein amino acid and has a plurality of important physiological functions, such as free radical removal, vasodilatation and blood pressure stabilization, moreover, the endogenous arginine (L-Arg) and NO can be continually generated through the L-cit-NO circulation in the human body to ensure the endosomatic arginine level to be obviously enhanced and to maintain at a higher foundation level simultaneously, thus, the hypoxia tolerance of the organism is enhanced.

L-ornithine is an important non-protein amino acid existing in tissues and cells and is also the precursor substance for metabolism of arginine, citrulline and other amino acids. L-ornithine almost participates in the entire processes of urea cycle activation and ammonia disintoxication, facilitates the synthesis of carbamyl phosphate synthetase and glutamine and increases the disintoxication function of the liver; therefore, L-ornithine is significant to the liver cells in the human body.

The *ginseng siccus* extract comes from the dried root and radix and *rhizomea ginseng* of *Panax ginseng* C.A Mey. or radix and rhizomea *ginseng* rubra Panaxoside. The main active ingredient, the *ginseng* extract can obviously protect the liver cell from chemical injury; the animal experiment proved that panaxoside can also protect the brain cell from the ischemia-reperfusion injury and has obvious improving effect on the chemical learning and memorization functional disorder of animals.

The *ginkgo siccus* extract comes from the folium *ginkgo* of *ginkgo biloba* L. The *ginkgo siccus* extract can prevent the abnormal metabolism of NO by reducing the $Ca^{2+}$ level, protects from the glutamate neurotoxicity, antagonizes the platelet activating factors and has the protective function on the brain tissue with hypoxic-ischemic encephalopathy, protects the liver and has transaminase reduction effects.

Silibinin, coming from the seed of *Silybum marianum* (L.), is a powerful free radical scavenger and an inhibitor of lipid peroxidation that has protective, healing and detoxification effects on the liver. Silibinin's activities on the enzyme enhancing and membrane stabilizing of the liver cell helps in reducing and repairing the damage to the liver that alcohol, a high fat diet, the tobacco consumption and many prescription medicines can causes.

The extract of *fructus lycii* comes from the *Fructus jujubae* of *Lycium barbarum* L. The *fructus lycii* is the usual traditional Chinese medicine for liver and kidney tonification, the color is scarlet and the flavor is sweet. Modern medical research have proven that the *fructus lycii* contains betaine, polysaccharide, crude fat, crude protein, carotene, vitamin A, vitamin C, vitamin B1, vitamin B2, calcium (C), phosphorus (P), Ferro (Fe), zinc (Zn), manganese (Mn), linoleic acid and other nutrient contents. Extract of *fructus lycii* has promotes the hematopoietic function and has anti-ageing, anti-mutation, anti-tumor, anti-fatty liver and blood glucose level reduction functions. The herbalist doctor often uses *fructus lycii* to treat Yin deficiency of liver and kidney, soreness and weakness of waist and knees, dizziness, morbid forgetfulness, blurred vision, hypopsia and overflow of tears, thirst quenching, spermatorrhea and other illness symptoms. For the people having a kidney deficiency, *fructus lycii* is undoubtedly a kind of healthcare nutriment. *Fructus lycii* is the optimum selection for health preservation from ancient time to modern time and has the life lengthening function.

Tea polyphenols is the general term of the polyphenol substances contained in the tea leaf, including flavanol class, anthocyanin class, anthoxanthin class, flavonol class, phenolic acid class and the like, wherein, the flavanol substance (catechin) is the most important. Tea polyphenols is also called tea tannide or tea tannin, which is the major component which forms the colour, smell and flavour of the tea leaf and is also the major component having the healthcare function in the tea leaf. Tea polyphenols has detoxification and radio resistance effects and can effectively block radio material from invading the bone marrow and can cause strontium (Sr) 90 and cobalt (Co) 60 to be quickly discharged from the body, therefore, it is honoured as Radiation Invincible Opponent and builds a defensive line for resisting to radiation injury for the health of human. The tea polyphenols have the cerebral stroke prevention, intestine and stomach tension relieving and digestion aiding functions and can clean the superfluous free radical in the human body, inhibit lipid peroxidation, enhance immunologic function and postpone senility.

Some compositions comprising herbs and/or other natural substances are already know from the prior art, this includes for example the compositions described in DATABASE TCM [Online] SIPO; 29 Oct. 2003 (2003 Oct. 29), Youmao Qi: "A pharmaceutical composition, and its usage" XP002585364 Database accession no. CN 1451426, or DATABASE TCM [Online] SIPO; 13 Oct. 2004 (2004 Oct. 13), Yiguo Liu et al: "A kind of rubber seed jelly" XP002585369 Database accession no. CN1 535617, as well as US 2005/01 9427 A1, or DATABASE TCM [Online] SIPO; 26 Jan. 2005 (2005 Jan. 26), Jinxue Cheng: "Oral functional Chinese medicine intensified by snake, bee, macroelement and microelement and its preparation" XP002585371 Database accession no. CN 1569123. Some other compositions are described in DATABASE TCM [Online] SIPO; 23 Nov. 2005 (2005 Nov. 23), Yimin Lin: "A product used for relieving alcoholic intoxication and protecting liver and its preparation method" XP002585357 Database accession no. CN 1698879, as well as WO 99/61 038 A1; DATABASE TCM [Online] 3 Dec. 1997 (1997 Dec. 3), Xiaolin Xia: "Composite of zinc containing compound and glutaminase/A pharmaceutical composition for the treatment of peptic ulcer" XP002585373 Database accession no. CN 1166320 as well as DE 19929993 A1, or DATABASE TCM [Online] 29 Jul. 1998 (1998 Jul. 29), Dahan Industry Corp.: "Hepatoprotective wine and process for preparation thereof" XP002585383 Database accession no. CN 1188800

However there is a still a need for an effective and safe composition for the treatment or the alleviation of alcohol intoxication.

SUMMARY OF THE INVENTION

Applicants have surprisingly discovered that the preparation according to the invention shows an interesting potential in alcohol detoxification. This safe natural preparation is particularly promising in the liver protection from chemical injury, the tolerance enhancement of hypoxy and the rapid decrease till elimination of the blood alcohol content.

Multiple functions and effects of the preparation according to the invention are simultaneously enhanced and strengthened. The preparation of the invention can avoid the alcoholic liver injury and can quickly reduce the ethanol content in the human body. Nowadays, drinking is a kind of social means and is also a kind of traditional living habit, there are more and more people with fatty liver or hepatocirrhosis resulting from long-term or excessive drinking, at the same time, driving after being intoxicated is also a kind of dangerous behaviour. After the preparation of the invention is administered orally in the corresponding time, extraordinary medical effect can be obtained to relieve the after-drinking and drunken phenomena.

In addition, due to the mutual synergic action among all components of the preparation of the invention, the phenomena of strength shortage, fatigability, emotional instability, aging and insomnia can be effectively overcome and the adaptability to environmental pollution, intensive competition, tense living tempo, overstrain brain working, unbalanced dietary structure and other aspects is strengthened.

In one aspect of the present invention there is provided a preparation comprising the combination of a composition (a) containing amino acids consisting of citrulline and ornithine hydrochloride and/or derivatives thereof and a composition (b) containing a mixture of *ginseng* or *ginseng* extract, *ginkgo biloba* leaf extract and silibinin extract, optionally with a suitable excipient.

In another aspect, the present invention provides for a dietary or food supplement, a food preparation, a beverage, and a medicament comprising the preparation of the present invention.

In a further aspect, the preparation of the present invention is provided for the treatment or the prevention of alcohol intoxication.

In a still further aspect, the present invention provides for a method of treating or preventing alcohol intoxication, chemical liver injury, hypoxic tolerance, in vivo ethanol content and reduction and viability enhancement in the anoxic environment comprising administering to a subject in need thereof an effective amount of the preparation or the medicament of the present invention.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular form "a", "an" and "the" include plural references unless the context clearly dictates otherwise.

The term "extract", as used herein includes any preparation obtained from plants, fruits or vegetables using an extraction method.

The term "food preparation" refers generally to material of either plant or animal origin, or of synthetic sources, that contain essential nutrients such as a carbohydrate, protein, fat, vitamin, mineral, etc. used in the body of an organism to sustain growth, repair, and vital processes and to furnish energy A "dietary or food supplement" refers to a product that contains substances like vitamins, minerals, foods, botanicals, amino acids and is intended to supplement the usual intake of these substances. Dietary supplements are found in pill, tablet, capsule, powder or liquid form and are meant to be taken by mouth.

The term "nutraceutical" refers to any substance that is a food or a part of a food and provides medical or health benefits, including the prevention and treatment of disease. Such products may range from isolated nutrients, dietary supplements and specific diets to genetically engineered designer foods, herbal products, and processed foods such as cereals, soups and beverages. It also refers to a product isolated or purified from foods, and generally sold in medicinal forms not usually associated with food and demonstrated to have a physiological benefit or provide protection against diseases like chronic diseases for example.

The term "beverage" means a liquid for drinking, which may be water, flavored water, soft drinks, alcoholic drink, health drink, or an enriched drink like based on a diary product (milk) or fruit juice.

"Pharmaceutically acceptable excipients or carriers" are any materials that do not interfere with the pharmacological activity of the active ingredient(s) or degrade the body functions of the subject to which it can be administered but facilitate fabrication of dosage forms or administration of the composition. Examples of pharmaceutically acceptable excipient include but are not limited to maltodextrin, calcium phosphate, and fused silica. Pharmaceutically acceptable excipients also include flavorants, as well as various additives such as other vitamins and minerals, all solvents, dispersion media, coatings, isotonic and absorption delaying agents, sweeteners and the like, non-toxic auxiliary substances such as wetting or emulsifying agents, pH buffering agents and the like, such as for example, sodium acetate, sorbitan monolaurate, triethanolamine oleate, and inert ingredients such as talc and magnesium stearate which are standard excipients in the manufacture of tablets, capsules and other dosage forms.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

The term "an effective amount" refers to an amount necessary to obtain a physiological effect. The physiological effect may be achieved by one application dose or by repeated applications. The dosage administered may, of course, vary depending upon known factors, such as the physiological characteristics of the particular composition; the age, health and weight of the subject; the nature and extent of the symptoms; the kind of concurrent treatment; the frequency of treatment; and the effect desired and can be adjusted by a person skilled in the art.

The Applicants have studied specific plants and several amino acids and their potential application in alcohol detoxification. Surprisingly it was found that the administration of the preparation according to the invention among other unexpected biological activities dramatically reduces the blood alcohol content in the body.

The synergy action of the preparation according to the invention seems to be separated by any other pharmacological action (see the Examples).

The present invention provides for a preparation comprising the combination of a composition (a) containing amino acids consisting of citrulline and ornithine hydrochloride and/or derivatives thereof and a composition (b) containing a mixture of *ginseng* or *ginseng* extract, *ginkgo biloba* leaf extract and silibinin extract, optionally with a suitable excipient.

According to the present invention, it is intended by citrulline and/or ornithine hydrochloride "derivatives" any structural as well as functional derivatives thereof. Derivatives thereof may be for example precursors of said amino acid as well as by products thereof (also defined as degradation products).

"Precursors of amino acids" are metabolites originated from metabolic pathways such as the glycolysis, the TCA cycle (tricarboxylic acid cycle) or the pentose phosphate pathway. More specifically these precursors include α-ketoglutarate, 3-phosphoglycerate, oxaloacetate, pyruvate, phosphoenolpyruvate and erythrose 4-phosphate, ribose 5-phosphate and any other molecule upstream or downstream of the way leading to these metabolic precursors. "Degradation products of amino acids" are amino acids that may undergo an initial degradation that removes amino group either by transamination or by oxidation. The ammonium ion is recovered and recycled to form another amino acid or eliminated. The carbon skeleton obtained after the removal of the amine group can also be recovered to synthesize the corresponding amino acid or as a precursor for the synthesis of carbohydrates (in the case of amino acids glycoforms) or converted into acetyl-CoA for fatty acid synthesis (i.e. ketogenic fatty acids).

Also encompassed by the definition of the terms derivatives of citrulline and/or ornithine hydrochloride are pharmaceutically acceptable salts thereof. According to the present invention, pharmaceutically acceptable salts are produced from acidic inorganic or organic compounds, or alkaline inorganic or organic compounds. As used herein, the phrase "pharmaceutically acceptable salt" refers to a salt that retains the biological effectiveness of the free acids and bases of a specified compound and that is not biologically or otherwise undesirable. The pharmaceutically acceptable salts of the amino acids according to the invention are acid addition salts with pharmaceutically acceptable acids.

A desired salt may be prepared by any suitable method known in the art, including treatment of the free base with an inorganic acid, such as hydrochloric acid, hydrobromic acid, sulphuric acid, nitric acid, phosphoric acid, and the like, or with an organic acid, such as formic acid, acetic acid, maleic acid, succinic acid, mandelic acid, maleic acid, fumaric acid, malonic acid, pyruvic acid, oxalic acid, glycolic acid, salicylic acid; a pyranosidyl acid, such as glucuronic acid or galacturonic acid; an alpha-hydroxy acid, such as citric acid or tartaric acid; an amino acid, such as aspartic acid or glutamic acid; an aromatic acid, such as benzoic acid or cinnamic acid; a sulfonic acid, such as methanesulfonic acid, p-toluenesulfonic acid or ethanesulfonic acid; or the like.

In the present invention the preferred ammonium salts are derived from hydrochloric, hydrobromic, methanesulfonic, acetic, propionic, benzoic, citric, tartaric, malic, maleic, fumaric, lactic, nitric, and phosphoric or succinic acid.

Generally, the salts are prepared by reacting the free base with stoichiometric amounts or with an excess of the desired salt forming inorganic or organic acid in a suitable solvent or various combinations of solvents. For example, the free base can be dissolved in a mixed aqueous solution of the appropriate acid and the salt recovered by standard techniques, for example, by evaporation of the solution. Alternatively, the free base can be charged into an organic solvent such as a lower alkanol, symmetrical or asymmetrical ethers containing 2 to 10 carbon atoms, an alkyl ester, or mixtures thereof, and the like, and then it is treated with the appropriate acid to form the corresponding salt. The salt is recovered by standard recovery techniques, for example, by filtration of the desired salt from the mixture, or it can be precipitated by the addition of a solvent in which the salt is insoluble and recovered there from.

Examples of suitable inorganic and organic solvents for performing the various reactions include any inorganic or organic solvent that does not adversely affect the reactants or the resulting product, including halogenated solvents such as methylene chloride, chloroform, ether solvents such as diethyl ether, and other solvents such as tetrahydrofuran, dioxane, diglyme, cyclooctane, benzene or toluene, heptane, cyclohexane, aliphatic as well as cycloaliphatic and aromatic hydrocarbon solvents, water, acidified aqueous solutions, mixed organic and inorganic solutions, ethyl acetate, propyl acetate and mixtures thereof.

Also encompassed by the present invention are salts formed from acidic prodrugs, such as phosphates, and alkaline inorganic or organic compounds. Preferred inorganic cations comprised in the salts are lithium, sodium, potassium, rubidium, ammonium, calcium, magnesium, zinc and manganese. Production of phosphate salts are described in e.g. G. R. Pettit et al. *Anti-Cancer Drug Design* 16 (2001) 185-193.

Usually salts also include those formed from acidic prodrugs and organic amines, including, but not limited to, imidazole and morpholine. Alkaline amino acid salts may also be used.

Preferred salts according to the invention are for example Citrulline Malate which is a combination of the amino acid citrulline and the organic salt malate: L-Citrulline DL-malate. As well as D-Citrulline (1) also known as: (R)-2-Amino-5-ureidopentanoic acid, DL-Citrulline (1) also know as: (±)-2-Amino-5-ureidopentanoic acid, DL-2-Amino-5-ureidovaleric acid; L-Citrulline (3) L-Citrulline 7-amido-4-methylcoumarin hydrobromide (1) also known as: L-Citrulline 4-methyl-7-coumarinylamide hydrobromide, L-Citrulline-4,4,5,5-d4 (1); N-2,4-DNP-DL-Citrulline (1); Thio-L-citrulline (2) or L-Citrulline monohydrochloride. Pharmaceutical salts of ornithine are also contemplated such as ornithine alpha-ketoisocaproate, ornithine alpha-ketoglutarate (O alpha KG), ornithine chlorhydrate.

The term "citrulline and/or ornithine hydrochloride derivatives" designates, according to the invention, in particular the [alpha]-amino acids occurring in nature, but moreover also includes their homologues, isomers, analogs all those terms are referred under the definition of derivatives as described above. Enantiomers can be mentioned as an example of isomers. Analogs can be, for example, amino acids provided with protective groups.

Furthermore, since an inherent problem with native peptides (in L-form) is the degradation by natural proteases, the amino acids of the invention may be prepared in order to include D-forms and/or "retro-inverso isomers" thereof.

A higher biological activity is predicted for the retro-inverso containing amino acid when compared to the non-retro-inverso containing analogue owing to protection from degradation by native proteinases. Furthermore they have been shown to exhibit an increased stability and lower immunogenicity [Sela M. and Zisman E., (1997) Different roles of D-amino acids in immune phenomena-*FASEB J.* 11, 449].

Retro-inverso amino acids are prepared as described for example in Sela and Zisman, (1997).

Also encompassed by the definition of derivatives are modifications of the "citrulline and/or ornithine hydrochloride" including in vivo or in vitro chemical derivatization, e.g., acetylation or carboxylation. Also included are modifications of glycosylation, e.g., those made by modifying the glycosylation patterns of an amino acid during its synthesis and processing or in further processing steps, e.g. mammalian glycosylating or deglycosylating enzymes. Also included are sequences which have phosphorylated amino acid residues, e.g., phosphotyrosine, phosphoserine, or phosphothreonine.

In the preparation according to the invention, no carrier or pharmaceutically acceptable carrier or suitable excipients are often required to be added. However, suitable excipients may optionally be added.

Examples of suitable excipients of this invention include, but are not limited to, anti-adherents, binders (e.g., macrocrystalline cellulose, gum tragacanth, or gelatin), coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof.

For example, the preparation of the present invention may include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

Optionally the preparation of the present invention may include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and combinations thereof.

The active substances in the preparation according to the invention, such as the concentration of the amino acids or the plant extracts can change within a wide range. It is advantageous that the weight of one active substance amounts to 1 percent to 90 percent of that of all the active substances in the preparation.

Preferably, composition (a) containing amino acids has a proportion by weight of citrulline and ornithine hydrochloride, and/or derivatives thereof being of 0.1 percent to 99 percent: 99 percent to 0.1 percent respectively.

Respectively, composition (b) has preferably a proportion by weight of *ginseng* or *ginseng* extract, *ginkgo biloba* leaf extract and silibinin extract being of 0.01 percent to 99 percent, 0.01 percent to 99 percent and 0.01 percent to 99 percent respectively.

In a particular embodiment of the invention, composition (a) containing amino acids further comprises additional amino acids selected among arginine, ornithine, threonine, tryptophan or 5-hydroxytryptophan and/or derivatives thereof (as defined above).

Preferably, the weight ratio between said added amino acids and composition (a) containing amino acids consisting of citrulline and ornithine hydrochloride and/or derivatives thereof is 0.0001 percent to 50 percent: 99.9999 percent to 50 percent respectively.

In a more particular embodiment of the invention, composition (b) further comprises additional plant extracts selected among barberry wolfberry fruit extract and tea polyphenols.

In this latter embodiment, the weight ratio of the preparation of the invention preferably comprises:
the mixture of *ginseng* or *ginseng* extract between 0.001 percent to 99 percent,
the *ginkgo biloba* leaf extract between 0.001 percent to 99 percent, the silibinin extract between 0.001 percent to 99 percent, the barberry wolfberry fruit extract between 0.0001 percent to 70 percent,
and the tea polyphenols respectively between 0.0001 percent to 60 percent.

The preparation according to the invention may be in the form of a solid formulation, such as capsules or tablets or in the form of a liquid or oil solution. The formulation of the preparation described in the present invention can be prepared through any known method in the healthcare food or pharmacological field.

Any method familiar to the skilled in the art can be adopted, that is to say, the composition prepared by amino acids and plant extracts is manufactured into a solid formulation, such as capsules and tablets, or a liquid formulation, such as oral liquid and oil solutions to be administered with or without suitable carrier system.

Preferably each manufactured capsule or tablet may contain per dosage unit:
  80 mg to 816 mg of citrulline or identical amount of the derivative thereof,
  50 mg to 512 mg of ornithine or identical amount of salt or the derivative thereof,
  0.0001 mg to 430 mg of arginine or identical amount of the derivative thereof,
  0.0001 mg to 310 mg of tryptophan or identical amount of the derivative thereof,
  0.0001 mg to 450 mg of 5-hydroxytryptophan or identical amount of the derivative thereof,
  0001 mg to 500 mg of threonine or identical amount of the derivative thereof,
  1 mg to 500 mg of *ginseng* extract, extract of *ginkgo biloba* leaf, extract of silibinin or barberry wolfberry fruit extract and,
  0.0001 mg to 250 mg of tea polyphenols.

As for oral administration for human, the recommended dosage of the invention may for example contain the preparation of 250 mg, 500 mg, 1000 mg, 1500 mg or 2000 mg per dosage unit respectively, the preparation can be taken twice or three times per day, and the dosage can be adjusted according to the age and weight of the user.

In the case of a medicament, the suitable excipient or carrier system can be also a pharmaceutically acceptable excipient.

Suitable carrier systems comprise flow aid, such as micropowder silicon gel and cornstarch, which can enhance the compressibility and can prevent from sticking. For example, hydroxypropyl cellulose, methylcellulose, methylcellulose, croscarmellose sodium, various amylum derivatives, silicon dioxide and any other disintegrating agents having the disintegration facilitating function such as tylose, cross-linked sodium carboxymethyl cellulose, various starch derivatives;

In addition, suitable carrier systems may also comprise anti-blushing agent, such as glyceryl behenate, which is helpful for enhancing moisture resistance capability.

Furthermore, suitable carrier systems may also comprise lubricant, such as magnesium stearate, French white and the like, having the lubrication function.

Preferably, the suitable carrier is selected among hydroxypropyl cellulose, methylcellulose, methylcellulose, croscarmellose sodium, various amylum derivatives, silicon dioxide, magnesium stearate, French white, glyceryl behenate and anti-blushing agent.

The present invention further provides for a food preparation, a dietary or food supplement, a nutraceutical, a beverage as well as a medicament comprising the preparation of the present invention. As described above, the medicament may further comprise a pharmaceutically acceptable excipient.

Preferably the medicament, the nutraceutical or dietary supplement of the present invention is administered at a dosage of between 0.1 mg/kg per day to 1 g/kg per day.

The preparation according to the invention can be used, in the:
  protection of chemical liver injury,
  hypoxic tolerance enhancement,
  in vivo ethanol content quickening removal and
  reduction and viability enhancement in the anoxic environment.

In particular the medicament of the invention can be used for the treatment or prevention of alcohol intoxication, as well as, chemical liver injury, hypoxic tolerance, in vivo ethanol content and reduction and viability enhancement in the anoxic environment.

The present invention also provides for a method of treating or preventing alcohol intoxication, as well as, chemical liver injury, hypoxic tolerance, in vivo ethanol content and reduction and viability enhancement in the anoxic environment comprising administering to a subject in need thereof an effective amount of the preparation or of the medicament of the present invention. The subject in need thereof is a mammal, preferably a human.

The preparation or the medicament is administered orally, parenterally or topically.

If intended for oral administration, the medicament of the present invention can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a solution for intravenous, intramuscular or subcutaneous injection.

The topical preparations according to the present invention can be, but not limited to, a cream, a patch, a gel, an ointment, a lotion, a tincture, a spray, a mousse, a cleansing composition or a foam. The topical preparations of the present invention can be also in the form of a suspension or dispersion in solvents or fatty substances, or alternatively in the form of an emulsion or micro emulsion, PET-emulsions, multiple emulsions, bickering emulsions, hydrogels, alcoholic gels, lipogels, one or multiphase solutions or a vesicular dispersion and other usual compositions, which can also be applied by pens, as masks or as sprays. The emulsions can also contain anionic, nonionic, cationic or amphoteric surfactant(s).

Surprisingly, it has been observed that the preparation of the invention is also effective in the treatment or prevention of headache or migraine.

A person suffering from headache can experience pain in several areas of the head, including a network of nerves that extends over the scalp and certain nerves in the face, mouth, and throat. The muscles of the head and the blood vessels found along the surface and at the base of the brain are also sensitive to pain because they contain delicate nerve fibers. The bones of the skull and tissues of the brain itself do not hurt because they lack painsensitive nerve fibers. The ends of these pain-sensitive nerves, called nociceptors, can be stimulated by stress, muscular tension, dilated blood vessels, and other headache triggers. Vascular headaches (such as migraines, for instance) are thought to involve abnormal function of the brain's blood vessels or vascular system; muscle contraction headaches appear to involve the tightening or tensing of facial and neck muscles; while traction and inflammatory headaches are symptoms of other disorders, ranging from brain tumor to stroke or sinus infection. Some types of headache are signals of more serious disorders: sudden, severe headache; headache associated with convulsions; headache accompanied by confusion or loss of consciousness; headache following a blow on the head; headache associated with pain in the eye or ear; persistent headache in a person who was previously headache free; recurring headache in children; headache associated with fever; headache that interferes with normal life.

Headaches are diagnosed as vascular, muscle contraction (tension), traction or inflammatory headaches.

The most common type of vascular headache is migraine. Migraine is the most common neurological condition in the developed world. It affects about 10% of the population and is more prevalent than diabetes, epilepsy and asthma combined. Migraine is more than just a headache. It can be a debilitating condition which has a considerable impact on the quality of life of sufferers and their families. Attacks can be completely disabling, forcing the sufferer to abandon everyday activities for up to 3 days. Even in symptom free periods, sufferers may live in fear of the next attack. The pain of a migraine headache is often described as an intense pulsing or throbbing pain in one area of the head. It is often accompanied by extreme sensitivity to light and sound, nausea, and vomiting. Migraine is three times more common in women than in men. Some individuals can predict the onset of a migraine because it is preceded by an "aura" visual disturbances that appear as flashing lights, zig-zag lines or a temporary loss of vision. People with migraine tend to have recurring attacks triggered by a lack of food or sleep, exposure to light or hormonal irregularities (only in women). Anxiety, stress or relaxation after stress can also be triggers. For many years, scientists believed that migraines were linked to the dilation and constriction of blood vessels in the head. Investigators now believe that migraine is caused by inherited abnormalities in genes that control the activities of certain cell populations in the brain. There are two ways to approach the treatment of migraine headache with drugs: prevention of the attacks or the relief of the symptoms during the attacks. Many people with migraine use both approaches by taking medications originally developed for epilepsy and depression to prevent future attacks, and treating attacks when they happen with drugs called triptans that relieve pain and restore function.

After migraine, the most common type of vascular headache is the toxic headache produced by fever. Pneumonia, measles, mumps, and tonsillitis are among the diseases that can cause severe toxic vascular headaches.

Toxic headaches can also result from the presence of foreign chemicals in the body.

Other kinds of vascular headaches include "clusters," which cause repeated episodes of intense pain, and headaches resulting from a rise in blood pressure. Cluster headaches, named for their repeated occurrence in clusters over weeks or months at roughly the same time of day or night, begin as a minor pain around one eye, eventually spreading to that side of the face. The pain quickly intensifies, compelling the victim to pace the floor or rock in a chair, for instance. Other symptoms include a stuffed and runny nose and a droopy eyelid over a red and weeping eye. Cluster headaches last between 30 and 45 minutes but the relief people feel at the end of an attack is usually mixed with dread as they await a recurrence. Clusters may mysteriously disappear for months or years. Many people have cluster bouts during the spring and fall. At their worst, chronic cluster headaches can last continuously for years. Cluster attacks can strike at any age but usually start between the ages of 20 and 40. Unlike migraine, cluster headaches are more common in men and do not run in families. Paradoxically, both nicotine, which constricts arteries, and alcohol, which dilates them, trigger cluster headaches. The exact connection between these substances and cluster attacks is not known.

In one embodiment of the invention, suppression of cortical spreading depression (CSD) has not been reported.

Thus, the present invention concerns the use of the preparation according to the invention for the prevention, alleviation or/and treatment of headache, especially chronic headache such as migraine. Further, the present invention concerns the use of the preparation according to the invention for the prevention, alleviation or/and treatment of all types of painful conditions associated with or/and caused by CSD, such as, but not limited to, cerebral ischemia during stroke or cardiovascular surgery, for instance, traumatic brain injury, subarachnoid haemorrhage or transient global amnesia. Preferred, but not limited to, is the use of the preparation of the invention for the prevention, alleviation or/and treatment of chronic headache associated with or/and caused by CSD such as migraine or other forms of chronic headache of both central and peripheral origin such as, but not limited to, cluster headache, tension-type headache or secondary headaches associated with over use of medication, cranial neuralgias, brain trauma and vascular or metabolic disorders, for example. Especially preferred is the treatment of acute migraine.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practising the present invention and are not intended to limit the scope of the invention.

EXAMPLES

In the following Examples, the *ginseng* extract, extract of *ginkgo biloba* leaf, barberry wolfberry fruit extract and extract of silibinin can be prepared according to the following methods.

*Ginseng* Extract: red *ginseng* is crushed, 70 percent of ethanol with eight-time quantity of the red *ginseng* is added, back flow extraction is performed twice and each extraction lasts for three hours, the extracted solution is combined, and the spray drying is performed after the extracted solution is condensed. A yellow white powder is obtained; the total *ginseng* ginsenoside content can not be less than 80 percent after being determined through UV spectrophotometry.

Extract of *Ginkgo Biloba* Leaf: the extract of *ginkgo biloba* leaf is manufactured according to the preparation method stipulated in Chinese Pharmacopoeia (2005 Edition) and conforms to Chinese Pharmacopoeia Quality Standard (2005 Edition). The preparation method as described in the Chinese Pharmacopoeia (2005 Edition) is as follows. *Gingko biloba* extract is the extract prepared from *Ginkgo* leaf. Pulverize *Ginkgo* leaf to powder, extract with diluted ethanol under reflux, combine the extracts, recover ethanol and concentrate to a quantity. Apply it to a previously prepared column of macroporous resin, elute stepwise with water and ethanol of different concentrations. Collect the ethanolic eluates, recover ethanol, spray to dryness, or concentrate to a thick extract, dry in vacuum and pulverize.

Barberry Wolfberry Fruit Extract: *fructus lycii* is extracted after being heated with water and then is condensed and deposited with alcohol to obtain the deposition, the barberry wolfberry fruit extract is obtained through degreasing, deproteinization, decolorization and drying. The extraction rate is 1:10, 1:15, 1:20 or 1:30.

The seed coat of *silybum marianum* is incubated with ethyl acetate for ultrasonic extraction during 3 hours before removing the extracted solution and this procedure is repeated 3 times.

The condensed is twice crystallized with ethanol before a recristalization with acetone-petrolemether (90:10) to obtain a silibinin at a concentration of 80-90%.

Example 1

The acute cerebral ischemia hypoxia survival time of the mice through different formulations is provided.

Dosage: 800 mg/kg per day per group. The test sample is prepared by redistilled water and drenched into the stomach through the mouth for seven days continuously.

Testing Method: The mice are respectively sacrificed one hour after the last stomach drenching, and the time from the sacrifice of the mice to the time when they stop gasping through mouths is recorded with a second counter.

TABLE 1

Effect of different formulations of the Composition on the survival time after hypoxia induced by Acute Cerebral Ischemia in Mice

| Sample No. | Citrulline % | Ornithine Hydrochloride % | Silibinin extract % | *Ginseng* Extract % | Extract of *Ginkgo Biloba* Leaf % | Gasp Stopping Time (seconds) |
|---|---|---|---|---|---|---|
| 1 | 100.0 | | | | | 12.6 |
| 2 | 67.0 | 33.0 | | | | 12.9 |
| 3 | 54.4 | 25.6 | 20.0 | | | 13.2 |
| 4 | 54.4 | 25.6 | | 20.0 | | 14.3 |
| 5 | 54.4 | 25.6 | | | 20.0 | 13.4 |
| 6 | 54.4 | 25.6 | 10.0 | 10.0 | | 16.8 |
| 7 | 54.4 | 25.6 | 10.0 | | 10.0 | 16.5 |
| 8 | 54.4 | 25.6 | | 10.0 | 10.0 | 16.2 |
| 9 | 54.4 | 25.6 | 10.0 | 5.0 | 5.0 | 17.8 |
| 10 | 54.4 | 25.6 | 5.0 | 10.0 | 5.0 | 17.5 |
| 11 | 54.4 | 25.6 | 5.0 | 5.0 | 10.0 | 16.8 |
| 12 | 0 | 0 | 0 | 0 | 0 | 12.7 |

Table 1: Effect of different formulations of the Composition on the survival time after hypoxia induced by Acute Cerebral Ischemia in Mice.

Example 2

The raw materials, extender and auxiliary material were respectively sieved with a screen of 80 meshes before mixture preparation. According to the formula proportion, the raw materials, such as citrulline, ornithine hydrochloride, *ginseng* extract, extract of *ginkgo biloba* leaf and extract of *ziziphus jujube* and auxiliary materials, such as glyceryl behenate and hydroxy propyl cellulose with the amount half of the formula ratio are weighed to be mixed for 10 to 15 minutes and 80 percent of ethanol solution is added for preparing soft material; the soft material is manufactured into particles through a screen with 16 meshes; the particles are dried under the temperature of 60 to 65 degrees; the particles are collated and are filled with the flow aid micro-powder silicon gel, the lubricant magnesium stearate and the left disintegrating agent hydroxy propyl cellulose, and then the mixture is evenly mixed, pressured into tablets and coated.

The coating material adopts the coating powder 85G60997 supplied by Shanghai Lekang Coating Technology Co., Ltd. The preparation method adopts the following steps: 1000 ml of deionised water is added into a clean open-top beaker, the stirring device is started up and the rotating speed is guaranteed to be 100 to 300 rpm. Under the condition of constant stirring speed, 180 g of coating material is slowly added to the end in five minutes. After adding, the original stirring speed is maintained, and the required coating liquid is obtained after being stirred for another 45 minutes.

Each tablet weight 600 mg and contains 272 mg of citrulline, 128 mg of ornithine hydrochloride, *ginseng* extract, extract of *ginkgo biloba* leaf, extract of silibinin and the like (see Table 2).

TABLE 2

| | Raw and Auxiliary Materials/1 tablet | Product Amount (mg) |
|---|---|---|
| Raw Material | Citrulline | 272 |
| | Ornithine Hydrochloride | 128 |
| | Extract of Silibinin | 50 |
| | Ginseng Extract | 25 |
| | Extract of *Ginkgo Biloba* Leaf | 25 |

TABLE 2-continued

| | Raw and Auxiliary Materials/1 tablet | Product Amount (mg) |
|---|---|---|
| Extender excipient | Hydroxy Propyl Cellulose | 45 |
| | Micropowder Silicon Gel | 40 |
| | Glyceryl Behenate | 5 |
| | Magnesium Stearate | 10 |
| | 80% of Ethanol | 10 |

Example 3

The disequilibrium experiment of the mice is carried out, and the mice which haven't fallen off from the Rota-rod within three minutes are divided into a control group and a testing group arbitrarily. For the testing group, 1200 mg/kg of the composition in the invention is administered for stomach drenching, while for the control group, 1200 mg/kg of normal saline is administered for stomach drenching. After 15 minutes, the mice of the control group and the testing group are drenched with 56 percent of Chinese distillate spirits for stomach drenching, and the stomach drenching dosage is 8 ml/kg. The mice of the control group and the testing group are respectively positioned into the Rota-rod type fatigue instruments at the speed of 15 rpm after being administered with ethanol for 10 min, 30 min, 90 min and 120 min with one mouse for each instrument, and the number of the mice which haven't fallen off from the Rota-rod within three minutes is recorded.

Conclusions: the significant difference was observed between two groups, the number of non-falling mice from the Rota-rod after composition intaking is surprisingly higher than that of the control group.

TABLE 3

| Group | Animal Number | Number of Mice not Falling off from the Rota-rod/3 min | | | |
|---|---|---|---|---|---|
| | | 10 min | 30 min | 90 min | 120 min |
| Control Group | 20 | 2 | 5 | 7 | 8 |
| Testing Group | 20 | 6 | 11 | 16 | 17 |

Example 4

The mice spontaneous activity experiment is carried out. The mice are divided into an administration group and a model group arbitrarily. 800 mg/kg of the composition and 9.0 g/L of sodium chloride injection fluid are respectively drenched into the stomachs of the mice. After fifteen minutes, all the mice are drenched with 18 ml/kg of 56 percent of Chinese distillate spirits for stomach drenching and are positioned into the spontaneous activity instruments after 20 min, 90 min and 120 min with one mouse for each instrument, and after one minute adaptation, the activity times within five minutes is recorded as the spontaneous activity index.

Conclusions: the two groups have distinct differences, and the spontaneous activity of the mice which are administered with the composition in the administration group is surprisingly higher than that of the model group.

TABLE 4

| Group | Animal Number | Spontaneous Activity Times/5 min | | |
|---|---|---|---|---|
| | | 20 min | 90 min | 120 min |
| Model Group | 10 | 31.15 ± 3.435 | 21.23 ± 2.412 | 40.11 ± 5.142 |
| Administration Group | 10 | 47.30 ± 5.115 | 23.40 ± 1.985 | 45.60 ± 4.099 |

Example 5

A mice anti-intoxication and intoxication treatment experiment is carried out. Anti-intoxication Experiment: twenty mice (male and female half and half) are fed for three days and are divided into an administration group and a model group, with ten mice in each group. The mice in each group are forbidden to eat and drink for six hours, for the administration group, 800 mg/kg of the composition is administered for stomach drenching, while for the model group, 9.0 g/L of sodium chloride injection fluid with the identical amount is drenched orally. After 15 minutes, all the mice in the two groups are drenched with 18 ml/kg of 56 percent of Chinese distillate spirits for stomach drenching, and the time required from the righting reflex loss to the righting reflex recovery of the mice is recorded.

Intoxication Treatment Experiment: the number of the mice, the group division and the experiment method are identical with the above experiment, however, the medicine drenching time and the liquor drenching time are exchanged, and the time required from the righting reflex loss to the righting reflex recovery of the mice is recorded.

Conclusions: the two groups have distinct differences, and the administration group is surprisingly better than the model group.

TABLE 5

| Group | Animal Number | Time Required from Righting Reflex Loss to Righting Reflex Recovery (min) | |
|---|---|---|---|
| | | Intoxication Treatment Experiment | Anti-intoxication Experiment |
| Model Group | 10 | 260.74 ± 28.18 | 256.72 ± 36.34 |
| Administration Group | 10 | 157.99 ± 29.45 | 127.17 ± 39.33 |

Example 6

The whole blood ethanol concentration of the mice is determined. Twenty mice are divided into a model group and an administration group, with ten mice in each group. The stomach drenching is firstly performed to the mice in the model group with 9.0 g/L of sodium chloride injection fluid with the volume identical with that of the treatment group; and the mice in the administration group are drenched with 1200 mg/kg of the composition. After 60 minutes, the mice of the two groups are all drenched with 16 ml/kg of 56 percent of Chinese distillate spirits. 0.1 ml of heparin sodium is added into each headspace vial with 5 ml, after 120 min of the liquor drenching, the mice of the two groups are sacrificed for drawing blood, 0.6 ml of blood is accurately drawn and transferred into the headspace vial with the liquid-transferring gun, 5 μl of normal butyl alcohol is added as internal standard, the blood is quickly sealed through a capping device and is evenly shaken and is gasified in water bath with the constant temperature of 80 degrees for 20 min, the upper-layer air in the headspace vial is drawn off with a glass syringe of 1 ml, gas chromatograph is filled to detect the ethanol content.

Conditions of Gas Chromatograph: RTX-5 chromatographic column, film thickness of 0.25 μm, column length of 30 m, inner diameter of 0.25 nm, column temperature of 40° C., sample injection temperature of 140° C., detector temperature of 200° C., supporting gas of N2, column flow rate of 2 ml/min, splitting ratio of 1:9.0, H2 pressure of 50 kPa and air pressure of 50 kPa.

Conclusions: the two groups have distinct differences, and the average ethanol content in whole blood in the administration group is surprisingly less than that of the model group.

TABLE 6

| Group | Animal Number | Average Ethanol Content in Whole Blood (g/L) |
| --- | --- | --- |
| Model Group | 10 | 0.543 ± 0.088 |
| Administration Group | 10 | 0.133 ± 0.024 |

Example 7

Liver and Stomach ADH (Alcohol Dehydrogenase) Determination

Twenty mice are divided into a treatment group and a model group, with ten mice in each group. The mice in each group are forbidden to eat and drink for 16 hours. The mice of the treatment group are drenched with 800 mg/kg of the composition, and the mice in the control group are drenched with 9.0 g/L of sodium chloride injection fluid with the identical amount. After 15 minutes, the stomachs of the mice in the two groups are drenched with 16 ml/kg of Chinese distillate spirits of 56 percent. After 120 min, the livers and the stomachs of the mice are taken out, the related reagent is prepared according to the instruction manuals of ADH Kit and Coomassie Brilliant Blue Protein Kit, the mass of the liver and the stomach of the mice is accurately weighed through a balance with millesimal precision, 9.0 g/L of sodium chloride injection fluid is added according to the mass specific volume of 1:10 and is prepared into the tissue homogenate of 100 g/L through a glass homogenizer and is centrifuged at the speed of 2500 r/min for 10 min, and the supernatant fluid is sucked through a micro-adding sample injector. The supernatant fluid is divided into two parts, one part is diluted into tissue homogenate through 9.0 g/L of sodium chloride injection fluid according to the proportion of 1:9, the ADH activity (number of units of the homogenate protein per mg (unit)) in the supernatant fluid is determined with a 7520 type ultraviolet spectrophotometer; and the other part is used for determining the protein content in the liver and stomach.

Conclusions: the two groups have distinct differences, and the ADH activity in the administration group is surprisingly higher than that of the model group.

TABLE 7

| Group | Animal Number | ADH Activity (U) Liver | ADH Activity (U) Stomach |
| --- | --- | --- | --- |
| Model Group | 10 | 22.778 ± 4.521 | 29.642 ± 8.131 |
| Administration Group | 10 | 34.232 ± 9.471 | 54.235 ± 14.857 |

Example 8

Human Body Alcohol Concentration Test-Air Blowing Method

There are ten men in the male group with the age between 20 and 29; there are ten women in the female group with the age between 20 and 29; alcohol concentration tests are preformed for three times in terms of not taking the composition, taking the composition 15 min before drinking and taking the composition immediately after drinking, and the dosage of the composition to be taken is 1200 mg per person each time. Each person takes 50 ml of 56 percent of Chinese distillate spirits each time, and the air breathed out from each person is determined through the alcohol concentration testing instrument in 15 min, 30 min, 45 min, 60 min, 90 min and 120 min after drinking.

Conclusions: the alcohol concentration of the person after the composition is taken is surprisingly less than that of the person who does not take the composition, the difference between the male group and the female group is not large, and the effect of the administration before drinking is better than that of the administration after drinking.

TABLE 8

Male Group

Items
Alcohol Concentration (Air Blowing Method) Average

| Testing Time | Without | Taking before Drinking | Taking Immediately after Drinking |
| --- | --- | --- | --- |
| 15(min) | 0.52 | 0.30 | 0.43 |
| 30(min) | 0.48 | 0.15 | 0.25 |
| 45(min) | 0.36 | 0.10 | 0.18 |
| 60(min) | 0.32 | 0.08 | 0.12 |
| 90(min) | 0.27 | 0.05 | 0.08 |
| 120(min) | 0.17 | 0.02 | 0.05 |

TABLE 9

Female Group

Items
Alcohol Concentration (Air Blowing Method) Average

| Testing Time | Without | Taking before Drinking | Taking Immediately after Drinking |
| --- | --- | --- | --- |
| 15(min) | 0.48 | 0.32 | 0.42 |
| 30(min) | 0.45 | 0.20 | 0.33 |
| 45(min) | 0.41 | 0.15 | 0.19 |
| 60(min) | 0.31 | 0.11 | 0.15 |
| 90(min) | 0.24 | 0.05 | 0.09 |
| 120(min) | 0.17 | 0.01 | 0.02 |

Example 9

Animal Normal Pressure Hypoxia Tolerance Function Enhancement Experiment Through the Composition of the Invention Experimental Animal: A hundred and forty four second grade healthy female mice of ICR species are selected and arbitrarily divided into four groups with 12 mice for each group according to the body weight.

Dosage Design: Three dosage groups with the dosage of 400 mg/kg/d (equivalent to ten times the recommended intaking amount for an adult per kilogram of the body weight per day), 800 mg/kg/d and 1200 mg/kg/d are designed, and simultaneously a normal control group is arranged. The test sample is prepared through double distilled water, 20 ml/kgb wt of dosage is drenched into the stomachs of the mice in each group per day for continuous 30 days. The double distilled water with identical amount is drenched into the stomachs of the mice in the normal control group.

Experimental Method: The mice are respectively positioned into the ground glass stoppered bottles with 250 ml (volume error of ±1 ml) filled with 5 g of soda lime one hour after the last stomach drenching, the bottle mouths are sealed by applying the mineral butter, and timing is immediately performed, by taking the breath stopping as the index, the hypoxia tolerance and survival time under normal pressure of the mice are observed and recorded, the homogeneity of variance of the initial data is performed through the SPSS statistical software, when the variance is homogeneous, the pair wise comparative statistics by taking the average number among many experimental groups and a control group is performed.

Experimental Result: The body weight and the survival time of the animal in each group before and after the experiment are shown in table 10.

It can be seen that there is no difference (P larger than 0.05) on the body weight of the animal before and after the experiment. Compared with the control group, the hypoxia tolerance survival time of the animal in the high dosage group is higher than that of the control group, thereby having remarkable differences (P less than 0.01).

TABLE 10

Influence of the Composition on Mice Normal Pressure Hypoxia Tolerance Survival Time (X ± S n = 12)

| Group | Intaking Dosage (mg/kg bw/d) | Body Weight (g) 0 d | Body Weight (g) 30 d | Survival Time (sec) | P |
|---|---|---|---|---|---|
| Control | 0 | 20.86 ± 1.00 | 29.92 ± 1.83 | 1403 ± 241 | — |
| Low Dosage | 400 | 20.89 ± 0.91 | 28.92 ± 1.24 | 1316 ± 149 | 0.376 |
| Medium Dosage | 800 | 20.92 ± 1.03 | 28.58 ± 1.38 | 1457 ± 207 | 0.576 |
| High Dosage | 1200 | 20.65 ± 1.17 | 28.75 ± 2.30 | 1691 ± 319 | 0.005 |

Example 10

Animal Sodium Nitrite Intoxication Survival Enhancement Experiment Through the Composition of the Invention Dosage Design: Three dosage groups with the dosage of 400 mg/kg/d (equivalent to ten times the recommended intaking amount for an adult per kilogram of the body weight per day), 800 mg/kg/d and 1200 mg/kg/d are designed, and simultaneously a normal control group is arranged. The test sample is prepared with double distilled water, 20 ml/kgb wt of dosage is drenched into the stomachs of the mice in each group per day for continuous 30 days. The double distilled water with identical amount is drenched into the stomachs of the mice in the normal control group.

Experimental Method: After the last stomach drenching for one hour, sodium nitrite (injection capacity of 0.1 ml/10 g (body weight) is respectively injected into the abdominal cavities of the mice in each group according to the dosage of 220 mg/kg bw, timing is immediately performed, and by taking the breath stopping as the index, the survival time of the mice is recorded.

Experimental Result: The body weight and the survival time of the animal in each group before and after the experiment are shown in Table 11. There is no difference (P>0.05) on the body weight of the animal in the two groups before and after the experiment, compared with the control group, the survival time of the mice in each dosage group is prolonged, but there is no significant difference (P>0.05).

TABLE 12

Influence of the composition of the invention on Mice Sodium Nitrite Intoxication Survival Time (X ± S n = 12)

| Group | Intaking Dosage (mg/kg bw/d) | Body Weight (g) 0 d | Body Weight (g) 30 d | Survival Time (sec) | P |
|---|---|---|---|---|---|
| Control | 0 | 20.73 ± 1.42 | 29.75 ± 1.81 | 1429 ± 212 | — |
| Low Dosage | 400 | 20.17 ± 1.32 | 29.92 ± 1.97 | 1532 ± 185 | 0.386 |
| Medium Dosage | 800 | 20.69 ± 1.15 | 28.92 ± 2.02 | 1623 ± 395 | 0.105 |
| High Dosage | 1200 | 20.79 ± 0.99 | 28.75 ± 1.86 | 1507 ± 308 | 0.510 |

Example 11

Animal Acute Cerebral Ischemia Hypoxia Survival Time Prolongation Experiment Through the Composition Dosage Design: Three dosage groups with the dosage of 400 mg/kg/d (equivalent to ten times the recommended intaking amount for an adult per kilogram of the body weight per day), 800 mg/kg/d and 1200 mg/kg/d are designed, and simultaneously a normal control group is arranged. The test sample is prepared with double distilled water, 20 ml/kgb wt of dosage is drenched into the stomachs of the mice in each group per day for continuous 30 days. The double distilled water with identical amount is drenched into the stomachs of the mice in the normal control group.

Experimental Method: The mice in each group are respectively sacrificed one hour after the last stomach drenching, and the time from the sacrifice of the mice to the time they stop gasping through mouths is recorded with a second counter.

The body weight of the animal before and after the experiment and the time from the sacrifice of the mice to the time they stop gasping through mouths are shown in Table 12. There is no difference (P larger than 0.05) on the body weight of the animal in the two groups before and after the experiment. Compared with all the other dosage groups, the time from the sacrifice of the animal to the time they stop gasping through the mouths of the control group is increased, and the gasp stopping time of the animals between the medium dosage group and the high dosage group has extremely surprising difference (P less than 0.01).

TABLE 12

Influence of the Composition on Small Mice Acute Cerebral Ischemia Hypoxia Survival Time (X ± S n = 12)

| Group | Intaking Dosage (mg/kg bw/d) | Body Weight (g) 0 d | Body Weight (g) 30 d | Survival Time (sec) | P |
|---|---|---|---|---|---|
| Control | 0 | 20.50 ± 1.04 | 29.53 ± 2.27 | 13.91 ± 1.37 | — |
| Low Dosage | 400 | 20.77 ± 1.06 | 29.75 ± 2.22 | 15.18 ± 1.07 | 0.062 |
| Medium Dosage | 800 | 20.99 ± 1.14 | 29.50 ± 1.09 | 17.40 ± 2.30 | 0.000 |
| High Dosage | 1200 | 20.89 ± 1.19 | 28.00 ± 1.35 | 16.40 ± 1.48 | 0.001 |

Example 12

Alcoholic Liver Injury Auxiliary Protection Function Experiment Through the Composition The intaking amount of the composition for human body is 2400 mg per person each day.

Experimental Animal: Fifty healthy second grade female mice of ICR species with the body weight between 18 and 22 g are selected and are arbitrarily divided into five groups with 10 mice for each group according to the body weight.

Dosage Design: Three sample dosage groups with the dosage of 200 mg/kg/d, 400 mg/kg/d (equivalent to ten times the recommended intaking amount for an adult per kilogram of the body weight per day) and 1200 mg/kg/d, a blank control group and a model control group are designed. The test objects in the sample dosage groups are prepared with double distilled water, the test objects in the blank control group and the model control group are administered with double distilled water, 20 ml/kgb wt of dosage is respectively drenched into the stomachs of the mice in each group per day for continuous 30 days. 10 ml/kg b.wt. of 65 percent of ethanol is respectively drenched into the stomachs of the mice in the model control group and the sample dosage groups after two hours after the test object is administered for the last time, double distilled water is administered into the mice in the blank control group, the animal are sacrificed after fasting for six hours for various biochemical index determination and liver pathological histology examination.

Experimental Method

Determination of Biochemical Index: 0.2 g of hepatic tissue is taken and is manufactured into liver homogenate. The liver homogenate is centrifuged at the speed of 3000 rpm for ten minutes, and then the supernatant liquid is removed. The TG content in the supernatant liquid of the homogenate is determined with a biochemistry instrument, and MDA, GSH and protein level in the supernatant liquid of the homogenate are manually determined according to the method provided in the reagent kit.

Liver Pathological Histology Examination: The left lobe of the liver is taken and is fixed with 4 percent of formaldehyde, and the liver is cut into pieces through paraffin and ice, dyed through HE and sudan III, examined through microscope and graded.

Data Treatment: The body weight of the mice, TG, MDA, GSH and other data are all measurement data, the normality test and the homogeneity test for variance is performed on the initial data through the SPSS statistical software, the data of MDA and TG are logarithmically transformed to ensure the data thereof to meet the requirement of the homogeneity of variance, then, the solvent analysis is performed through the method of one-factor analysis of variance (ANOVA), the statistical treatment to the data (P is larger than 0.05) is performed through the pair wise comparative statistics by taking the average number between many experimental groups and a control group. The pathological histology inspection result is statistically treated through a rank sum test.

Experimental Result: The influence of the composition to the body weight of animals is shown in Table 14.1. There is no real difference (P larger than 0.05) on the body weight of the mice in all groups before and after the experiment. This shows that the composition has no particular influence on the body weight increases of the mice.

Table 14.2 shows the influence of the composition on the malondialdehyde (MDA) content in the liver homogenate of the mice. As shown in this Table, MDA content in the liver homogenate of the mice in the model control group is increased and has significant difference (P less than 0.01) compared with the blank control group, and this shows that modelling is successful. In the composition, compared with the model control group, the MDA in the liver homogenate of the mice in the high dosage group is decreased and has important difference (P less than 0.05), and this shows that the MDA content in the liver homogenate of the mice with the alcoholic liver injury in the high dosage group can be reduced by adopting the composition of the invention.

Table 14.3 shows the influence of the composition according to the invention on the reduced glutathione (GSH) content in the liver homogenate of the mice. Indeed the GSH content in the liver homogenate of the mice in the model control group is reduced and has significant difference (P less than 0.01) compared with the blank control group, and this shows that modelling is successful. Compared with the model control group, the GSH content in the liver homogenate of the mice in all the dosage groups is enhanced by adopting the composition of the invention, and the differences are respectively significant (P less than 0.05, P less than 0.01. This shows that the composition of the invention can enhance the GSH content in the hepatic tissue of the mice with an alcoholic liver injury.

Table 14.4 shows the influence of the composition according to the invention on the glycerin trilaurate (YG) content in the liver homogenate of the mice.

As shown in the Table 14.4, the TG content in the liver homogenate of the mice in the model control group is increased and has significant difference (P less than 0.01) compared with the blank control group, and this shows that modelling is successful. Compared with the model control group, the TG content in the liver homogenate of the mice in the high dosage group is reduced by adopting the composition and has significant difference (P less than 0.01), and this shows that the composition can reduce the TG content in the liver homogenate of the mice with the alcoholic liver injury in the high dosage group.

Table 14.5 shows the influence of the composition according to the invention on the pathologic change of the hepatic tissue of the mice. The hepatic cell fatty degeneration with different degrees of the mice is generated in the model control group and has significant difference (P less than 0.01) compared with the blank control group, and this shows that modelling is successful. Compared with the model control group, the hepatic cell fatty degeneration degree of the mice in all the dosage groups is reduced by adopting the composition of the invention and has significant difference (P less than 0.01). This shows that the composition can reduce the hepatic cell fatty degeneration degree of the mice with the alcoholic liver injury in all the dosage groups.

TABLE 14.1

Initial Body Weight and Final Body Weight of Each Mice ($\bar{X} \pm s$)

| Group | Dosage (mg/kg · wt · d) | Animal Number | Initial Body Weight (g) | Final Body Weight (g) | P |
|---|---|---|---|---|---|
| Control Group | 0 | 10 | 21.2 ± 1.2 | 27.6 ± 1.9 | 0.911 |
| Model Group | 0 | | 20.9 ± 1.4 | 27.9 ± 1.9 | 0.911 |
| High Dosage | 1200 | 10 | 20.9 ± 1.3 | 28.2 ± 2.2 | 0.911 |
| Medium Dosage | 400 | 10 | 20.8 ± 1.4 | 27.8 ± 1.8 | 0.911 |
| Low Dosage | 200 | 10 | 21.0 ± 1.3 | 27.8 ± 1.8 | 0.911 |

Notes:
The initial body weight p of the mice in each group is equal to 0.996 through ANOVA; and the final body weight p of the mice is equal to 0.911 through ANOVA.

TABLE 14.2

Influence of the Composition on Malondialdehyde (MDA) Content in Mice Liver Homogenate ($\bar{X} \pm s$)

| Group | Dosage (mg/kg · wt · d) | Animal Number | MDA (nmol/mg prot) | P Value |
|---|---|---|---|---|
| Blank Control Group | 0 | 10 | 3.8 ± 0.9 | 0.000 |
| Model Control Group | 0 | 10 | 9.5 ± 1.4 | — |
| High Dosage Group | 1200 | 10 | 6.5 ± 3.0 | 0.035 |
| Medium Dosage Group | 400 | 10 | 6.0 ± 1.6 | 0.020 |
| Low Dosage Group | 200 | 10 | 8.6 ± 2.8 | 0.782 |

Notes:
Data in each group is logarithmically transformed to obtain the result of P larger than 0.001 through ANOVA.

TABLE 14.3

Influence of the Composition on Glutathione (GSH) Content in Mice Liver Homogenate ($\bar{X} \pm s$)

| Group | Dosage (mg/kg · wt · d) | Animal Number | GSH (mg/g prot) | P Value |
|---|---|---|---|---|
| Blank Control Group | 0 | 10 | 104.458 ± 9.33 | 0.000 |
| Blank Control Group | 0 | 10 | 104.458 ± 9.33 | 0.000 |
| Model Control Group | 0 | 10 | 81.30 ± 10.02 | — |
| High Dosage Group | 1200 | 10 | 99.55 ± 10.85 | 0.000 |
| Medium Dosage Group | 400 | 10 | 89.71 ± 8.47 | 0.045 |
| Low Dosage Group | 200 | 10 | 93.22 ± 6.16 | 0.005 |

Notes:
Data P in each group is equal to 0.000 through ANOVA.

TABLE 14.4

Influence of the Composition on Glycerin Trilaurate (YG) Content in Small Mice Liver Homogenate ($\bar{X} \pm s$)

| Group | Dosage (mg/kg · wt · d) | Animal Number | TG (umol/g Liver) | P Value |
|---|---|---|---|---|
| Blank Control Group | 0 | 10 | 16.78 ± 1.22 | 0.000 |
| Model Control Group | 0 | 10 | 16.40 ± 7.85 | — |
| High Dosage Group | 1200 | 10 | 9.98 ± 2.62 | 0.006 |
| Medium Dosage Group | 400 | 10 | 12.76 ± 3.90 | 0.173 |
| Low Dosage Group | 200 | 10 | 15.36 ± 5.02 | 0.890 |

Notes:
Data P in each group is equal to 0.000 through ANOVA.

TABLE 14.5

Influence of the Composition on Pathologic Change of Small Mice Hepatic Tissue

| Group | Dosage (mg/kg · wt · d) | Animal Number | Liver Cytolipin Content Grading | | | | P value (Mann-Whitney Test) |
|---|---|---|---|---|---|---|---|
| | | | 0 | 1 | 2 | 3 | |
| Blank Control Group | 0 | 10 | 10 | 0 | 0 | 0 | <0.001 |
| Model Control Group | 0 | 10 | 0 | 2 | 7 | 1 | — |
| High Dosage Group | 1200 | 10 | 2 | 7 | 1 | 0 | <0.001 |
| Medium Dosage Group | 400 | 10 | 2 | 6 | 2 | 0 | <0.001 |
| Low Dosage Group | 200 | 10 | 0 | 6 | 3 | 1 | 0.001 |

Notes:
Data P in each group is less than 0.001 through the Kruskal-Wallis rank sum test and the examination.

To sum up the experimental results, four indexes of the liver MDA, GSH and TG contents and the pathological histology examination are positive by adopting the composition of the invention. This confirms that the composition of the invention presents an auxiliary protection function for the alcoholic liver injury.

Example 13

The composition according to the present invention was also tested in 8 volunteers suffering from recurrent migraine and it has been shown to decrease the frequency, the intensity and the duration of the migraine episodes as reported by the subjects following intake of the composition daily for 3 months.

The invention claimed is:

1. A method of treating or reducing alcohol intoxication, chemical liver injury, hypoxia associated with cerebral ischemia and improving hypoxia tolerance in an anoxic environment, comprising:
   administering to a subject in need thereof an effective amount of a preparation including a composition (a) containing amino acids consisting of citrulline and ornithine hydrochloride and/or pharmaceutically acceptable salts thereof and a composition (b) containing a mixture of an ethanolic extract of *ginseng*, a *Ginkgo biloba* leaf extract, and an ethyl acetate extract of *Silybum marianum* seed coat or silibinin, optionally with a suitable excipient, wherein:
   the composition (a) has a proportion by weight of citrulline and ornithine hydrochloride and/or pharmaceutically acceptable salts thereof of 99 to 0.1:0.1 to 99;
   the composition (b) has a proportion by weight of the ethanolic extract of *ginseng*, the *ginkgo biloba* leaf extract, and the ethyl acetate extract of *Silybum marianum* seed coat or silibinin of 0.01% to 99%, 0.01% to 99%, and 0.01% to 99%, respectively;
   the preparation is administered at a dosage of 200 mg/kg per day to 1200 mg/kg per day, and
   wherein the *Ginkgo biloba* leaf extract is obtained by pulverizing *ginkgo* leaf to powder, extracting with diluted ethanol under reflux, combining the extracts, recovering and concentrating the ethanol, applying it to a previously prepared column of macroporous resin, eluting stepwise with water and ethanol of different concentrations, collecting the ethanolic eluates, recovering ethanol, spraying to dryness, or concentrating to a thick extract, and drying in vacuum and pulverizing.

2. The method of claim 1, wherein the preparation is administered orally, parenterally or topically.

3. The method of claim 1, wherein the subject in need thereof is a mammal.

4. The method of claim 3, wherein the mammal is a human.

5. A method of treating or reducing hypoxia associated with cerebral ischemia, comprising:
   administering to a subject in need thereof an effective amount of a preparation including a composition (a) containing amino acids consisting of citrulline and ornithine hydrochloride and/or pharmaceutically acceptable salts thereof and a composition (b) containing a mixture of an ethanolic extract of *ginseng* and an ethyl acetate extract of *Silybum marianum* seed coat or silibinin, optionally with a suitable excipient, wherein:
   the composition (a) has a proportion by weight of citrulline and ornithine hydrochloride and/or pharmaceutically acceptable salts thereof of 99 to 0.1:0.1 to 99;
   the composition (b) has a proportion by weight of the ethanolic extract of *ginseng* and the ethyl acetate extract of *Silybum marianum* seed coat or silibinin of 0.01% to 99% and 0.01% to 99%, respectively; and
   the preparation is administered at a dosage of 200 mg/kg per day to 1200 mg/kg per day.

6. The method of claim 5, wherein the preparation is administered orally, parenterally or topically.

7. The method of claim 5, wherein the subject in need thereof is a mammal.

8. The method of claim 7, wherein the mammal is a human.

* * * * *